US00PP36877P2

(12) United States Plant Patent
Horvath

(10) Patent No.: US PP36,877 P2
(45) Date of Patent: Aug. 5, 2025

(54) ***ALLIUM* HYBRID PLANT NAMED 'New Moon'**

(50) Latin Name: ***Allium* hybrid**
Varietal Denomination: New Moon

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 18/445,817

(22) Filed: Feb. 20, 2024

(51) Int. Cl.
*A01H 5/02* (2018.01)
*A01H 6/04* (2018.01)

(52) U.S. Cl.
USPC ..... Plt./263.1
CPC ..... *A01H 6/04* (2018.05)

(58) Field of Classification Search
USPC ..... Plt./263.1
CPC ..... A01H 6/04; A01H 5/02
See application file for complete search history.

*Primary Examiner* — Keith O. Robinson

(57) ABSTRACT

A new, distinct *Allium* hybrid plant as shown and described, characterized by gray green foliage in combination with light purple flowers, on 39 cm stems.

2 Drawing Sheets

Figure 1:
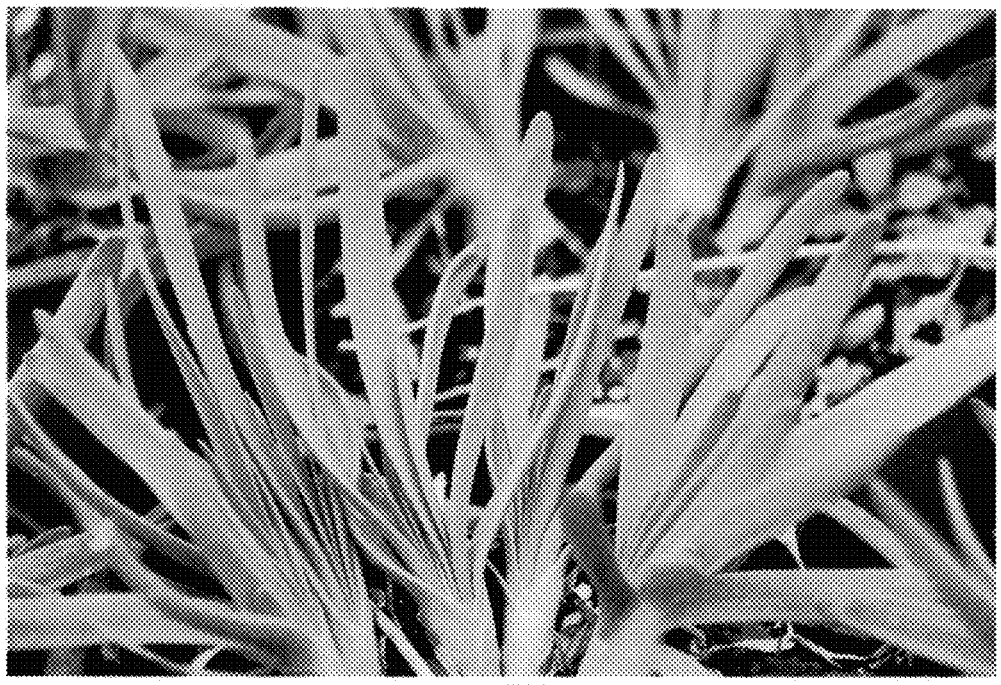

Latin name: *Allium* hybrid.
Cultivar name: 'New Moon'.

BACKGROUND OF THE INVENTION

The present invention relates to a new and distinct hybrid of *Allium* hybrid plant named 'New Moon' characterized by gray green foliage in combination with light purple flowers, on 39 cm stems. The new *Allium* hybrid was the result of a breeding program taking place in Hebron, IL since 2010. 'New Moon' arose as a selection from seed sown from open pollination of unnamed plants of *Allium*. The exact parentage of *Allium* hybrid 'New Moon' is unknown, however the female or seed parent is believed to be *Allium senescens* ssp. *glaucum*, while the male pollen parent is unknown. The selection of the new plant was due to its' gray green foliage in combination with light purple flowers, on 39 cm stems. Asexual division propagation has been the means of reproduction. The initial cutting and division propagation has taken place at a nursery in Hebron, IL in 2020. The new *Allium* has shown to be stable and identical in reproduction to the parent after dividing over 1000 plants from 2020 to 2023. No plants of the new *Allium* hybrid have been sold in this country, or anywhere in the world, prior to the filing of this application, nor has any disclosure of the new plant been made prior to the filing of this application with the exception of that which was disclosed within one year of filing of this application and was either derived directly or indirectly for the inventor. The first actual sale date of the plant was Apr. 20, 2023.

SUMMARY OF THE INVENTION

The new *Allium* hybrid plant named 'New Moon' characterized by gray green foliage in combination with light purple, on 39 cm stems, have been observed to be unique and stable.

Plants of the new *Allium* hybrid plant named 'New Moon' can be compared to *Allium* hybrid 'Summer Beauty', not patented. 1. The new plant height is typically 39 cm tall while *Allium* hybrid 'Summer Beauty' is typically 45 cm tall. 2. The new plant also has wider gray green foliage measuring 10 mm wide, RHS color 137 B while *Allium* hybrid 'Summer Beauty', has green foliage measuring 15 mm wide. 3. The new plant also has flowers RHS color 85 B and 85 C, while *Allium* hybrid 'Summer Beauty', pink flowers, RHS color not measured.

Plants of the new *Allium* hybrid plant named 'New Moon' can also be compared to plants of *Allium senescens* ssp. *glaucum* not patented. 1. The new plant height is typically 39 cm tall while *Allium senescens* ssp. *glaucum* is typically 20 cm tall. 2. The new plant also has gray green foliage measuring 10 mm wide, RHS color 137 B while *Allium senescens* ssp. *glaucum*, has thinner gray green foliage measuring 8 mm wide.

Plants of the new *Allium* hybrid plant named 'New Moon' can also be compared to plants of *Allium* hybrid 'Millenium' not patented. 1. The new plant height is typically 39 cm tall while *Allium* hybrid 'Millenium' is typically 50 cm tall. 2. The new plant also has gray green foliage measuring 10 mm wide, RHS color 137 B while hybrid 'Millenium', has bright green foliage measuring 15 mm wide.

DESCRIPTION OF PHOTOGRAPHS

FIG. 1. Foliage in April on a 2 year old plant in Hebron, IL USA.

Figure 2:
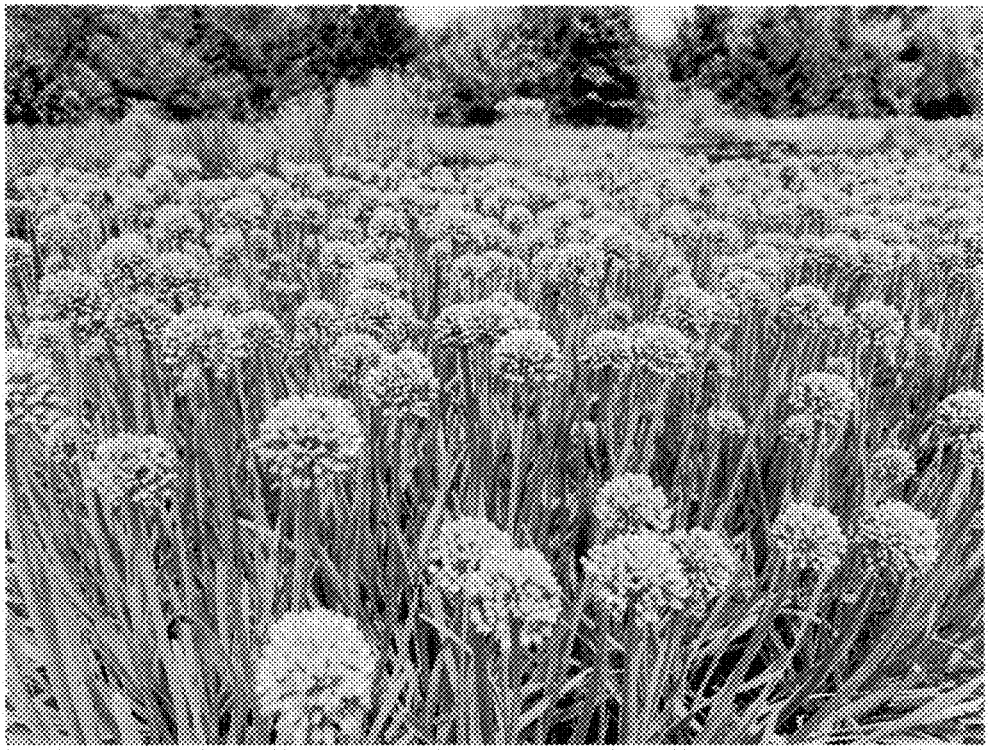

FIG. 2. Budding plants in July on a 2 year old plant in Hebron, IL USA.

Figure 3:
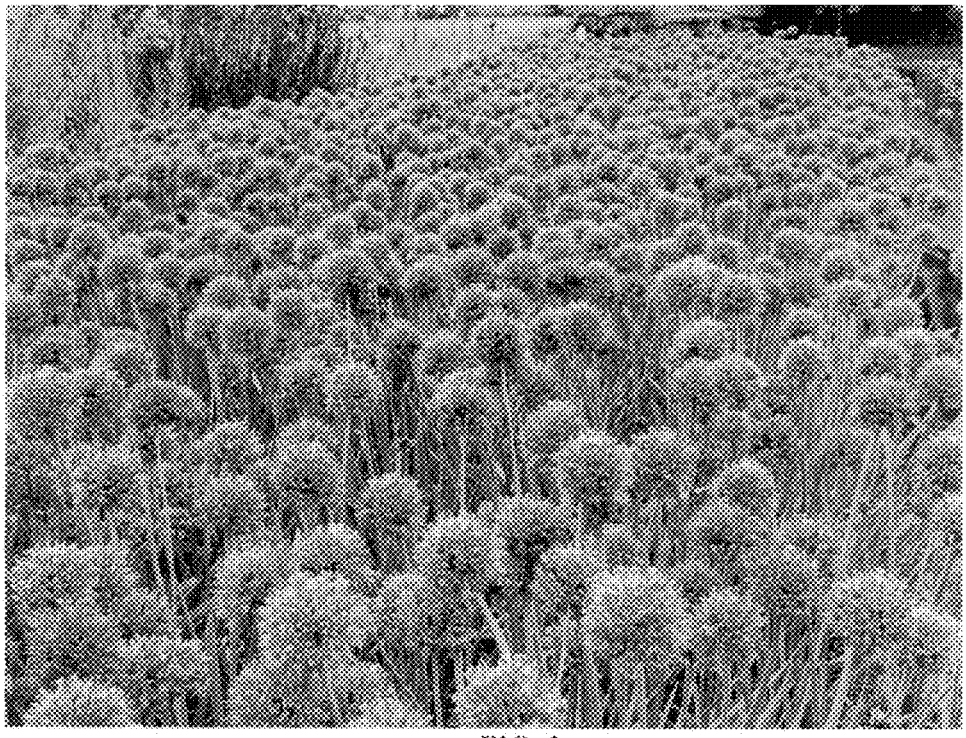

FIG. 3. Blooming plants in August on a 2 year old plant in Hebron, IL USA.

DETAILED BOTANICAL DESCRIPTION

In the following description, color references are made to The Royal Horticultural Society Colour Chart (2001). Plants used for the description were grown in a three gallon container for two years at a nursery in Hebron, Illinois. Measurements and numerical values represent averages of typical plants.

Botanical classification: *Allium* hybrid cultivar 'New Moon'.

Parentage: Female/seed parent. An open pollinated *Allium senescens* ssp. *glaucum* male parent an unknown *Allium*.

Propagation: Vegetative division.

Plant description:

*Type*.—Herbaceous perennial. The overall habit of the new *Allium* hybrid is a basal tuft of grey-green linear foliage arising from bulbous roots, with terminal light purple flower clusters in August.

*Hardiness*.—USDA zones 3-8.

*Plant height*.—39 cm.

*Plant width*.—40 cm.

Stem description:

*Stem shape*.—Round with ridges, solid.

*Stem size*.—Diameter — up to 4 mm at the widest by 2 mm at the thinnest.

*Stem length*.—39 cm.

*Internodes*.—None.

*Stem coloration*.—Stem color 137 C, color 137 D at the base.

*Stem texture*.—Ridged, smooth, and glabrous.

*Roots*.—Fibrous below the bulb, color 156 D.

*Bulb*.—Size — 13 mm wide at the base, 6 mm wide at the top where the foliage begins, 20 mm in length, color: 155 D. Bulb shape — conical to oblongoid.

Foliage description:

*Shape*.—Linear.

*Arrangement*.—Basal, alternate.

*Leaf blade size*.—Length: up to 22 cm, Width: 10 mm.

*Margins*.—Entire.

*Petiole*.—None.

*Leaf apex*.—Acute.

*Leaf base*.—Attenuate.

*Leaf quantity*.—An average of 10 per bulb.

*Texture*.—Upper and lower surfaces: smooth, glabrous.

*Adaxial and abaxial emerging leaf color description*.—137 B.

*Adaxial and abaxial mature leaf color description*.—137 B.

*Venation pattern*.—Parallel.

*Venation color*.—Upper 137 B, lower 137 B.

Flower description:

*Inflorescence type*.—Umbel, round, held on a leafless stalk.

*Umbel size*.—Length: 14 mm tall, width: 50 mm.

*Peduncle size and color*.—Length: 14 mm, diameter: less than 1 mm, color — 137 C.

*Peduncle texture*.—Smooth, glabrous.

*Pedicel size and color*.—Length: 14 mm, diameter: less than 1 mm, color — 137 C.

*Flower bud*.—Size: length: 25 mm, diameter: 30 mm.

*Flower bud surface*.—Smooth, glabrous.

*Flower bud shape*.—Ovoid, tubular, constricted at the base.

*Flower bud color*.—Between 85 B, 85 C, 85 D.

*Corolla description*.—3 petals unfused, constricted at the base.

*Petal apex*.—Entire, acute.

*Petal base*.—Unfused.

*Petal margin*.—Entire.

*Petal texture*.—Outer surface: smooth, inside surface: smooth.

*Petal color*.—Outer surface — color is 85 B and 85 C, inside surface — color is 85 B.

*Calyx shape*.—Stellate.

*Calyx size*.—Length: 7 mm, Width: 3 mm.

*Calyx color*.—85 D.

*Sepal quantity and arrangement*.—3, unfused.

*Sepal size*.—Length: 7 mm, diameter: 3 mm at base coming to a point.

*Sepal shape*.—Lanceolate, apex: acute, base: cuneate, margin: entire.

*Sepal texture*.—Upper and lower surfaces: smooth, glabrous.

*Sepal color*.—Adaxial color 85 B and 85 C, Abaxial color 85 C and 85 D.

*Flower type and shape*.—Bowl, comprised of 3 sepals and 3 petals.

*Flower color*.—85 B outside, 85 B and 85 C inside.

*Flower size*.—Length: 8 mm, width: 8 mm.

*Flower number*.—150 per umbel, 2900 per plant with up to 20 flowering stems.

*Bloom period and duration*.—3-4 weeks the middle of August in Hebron, IL.

*Flower longevity and duration on the plant*.—Approximately 3 weeks.

*Flower longevity and duration cut*.—Not measured.

*Scent*.—None.

Reproductive organs:

*Stamen*.—Quantity: 6, length: 11 mm, diameter: less than 1 mm at the base getting thinner toward the tip.

*Anther*.—Quantity: 6, length: 2 mm, diameter: 1 mm.

*Anther shape*.—Oval, color between N155 B.

*Filament*.—N155 B at tip near anther 155 A colored at the base.

*Pollen*.—Sparse, color: N155 B.

*Pistil*.—Number: 1, length: 5 mm, width: 1 mm, color — N155 B.

*Stigma shape*.—Conical, color — N155 B.

*Style*.—Number: 1, length: 4 mm, width 1 mm.

*Ovaries*.—Made of 3 carpels, length: 4 mm, width: 2 mm.

*Fruit*.—Capsule more or less round, 4 mm long, 3 mm wide, glabrous, color brown-black 202 A.

Disease resistance: Resistance to diseases common to *Allium* has not been observed on plants grown under nursery conditions.

I claim:

1. A new and distinct *Allium* hybrid plant named 'New Moon' as shown and described herein, characterized by wide gray green foliage in combination with light purple flowers, on 39 cm stems.

* * * * *